United States Patent [19]
Gibson et al.

[11] Patent Number: 5,269,181
[45] Date of Patent: Dec. 14, 1993

[54] APPARATUS AND PROCESS FOR MEASURING MECHANICAL PROPERTIES OF FIBERS

[76] Inventors: Ronald F. Gibson, 22594 Nottingham La., Southfield, Mich. 48034; Rangarajan Thirumalai, 2465 Somerset Blvd. Apt. #107, Troy, Mich. 48084; Rajiv Pant, 307 Cherry Valley Dr. Apt. P-25, Twister, Mich. 48141

[21] Appl. No.: 886,079

[22] Filed: May 20, 1992

[51] Int. Cl.$^5$ .................. G01N 27/00; G01N 29/00; G01H 17/00
[52] U.S. Cl. ........................................ 73/160; 73/579
[58] Field of Search ................................. 73/579, 160

[56] References Cited

U.S. PATENT DOCUMENTS

| | | | |
|---|---|---|---|
| 3,058,343 | 10/1962 | Hutchens et al. | 73/160 |
| 3,141,329 | 7/1964 | Canning | 73/160 |
| 3,486,369 | 12/1969 | Korzilius | 73/160 |
| 3,987,665 | 10/1976 | Hansen | 73/159 |
| 4,060,965 | 12/1977 | Schwartz | 73/160 |
| 4,133,207 | 1/1979 | Weidmann et al. | 73/160 |
| 4,584,875 | 4/1986 | Woo et al. | 73/160 |

FOREIGN PATENT DOCUMENTS

| | | | |
|---|---|---|---|
| 0134067 | 3/1960 | U.S.S.R. | 73/160 |
| 1647353 | 5/1991 | U.S.S.R. | 73/160 |

OTHER PUBLICATIONS

Leary, B., "The Design and Construction of a Vibrating String Evenness Tester for Textile Yarns," Instrument Practice, pp. 1179–1187 (Nov. 1958).
Kawabata, S., "Measurements of Anisotropic Mechanical Prop. & Thermal Conductivity of Single Fiber for Several High Performance Fibers", 253–262, Proc. 4th Japan. U.S. Conference on Composite Materials, Technomic Pub. Co., Lancaster, Pa. (1989).
DiCarlo, J. A. & Williams, W., "Dynamic Modulus & Damping of Boron, Silicon Carbide & Alumina Fibers", NASA TM 81422:E345 (1980).
Gibson, et al, "Development of an Apparatus to Measure Dynamic Modulus & Damping of Reinforced Fibers at Elevated Temperature", Soc. for Exper. Mech, Inc. Jun. 9–12, 1991.

*Primary Examiner*—William A. Cuchlinski, Jr.
*Assistant Examiner*—Diego F. F. Gutierrez
*Attorney, Agent, or Firm*—Brooks & Kushman

[57] ABSTRACT

A process and apparatus for measuring mechanical properties of structural fibers. The process comprises the steps of suspending at least one fiber from a rigid fixture so that it may hang vertically therefrom; attaching a mass to the fiber, thereby placing the fiber in tension; guiding the mass in a frictionless manner to avoid extraneous damping so that only extensional motion is permitted; exciting the mass and the fiber with a longitudinally directed impulse to induce an amplitude of extensional vibration; generating output signals according to the impulse and the vibration response; and communicating computing means with the output signals. The computing means stores data for deriving certain material properties of the fiber based upon the output signals and computes the material properties.

12 Claims, 5 Drawing Sheets

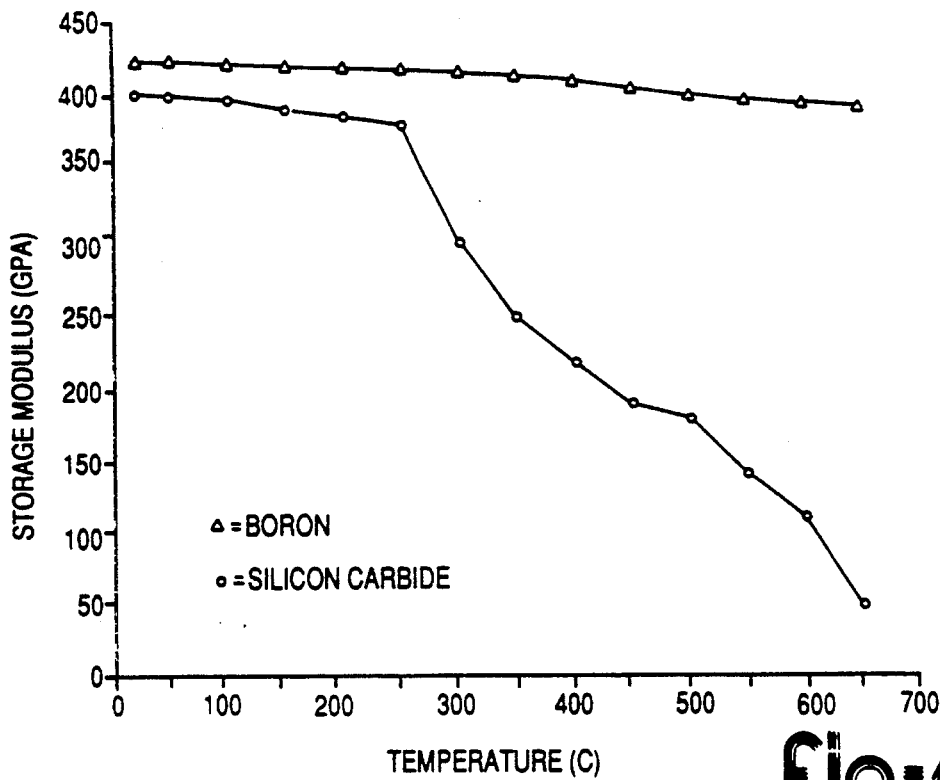
fig-4
fig-5
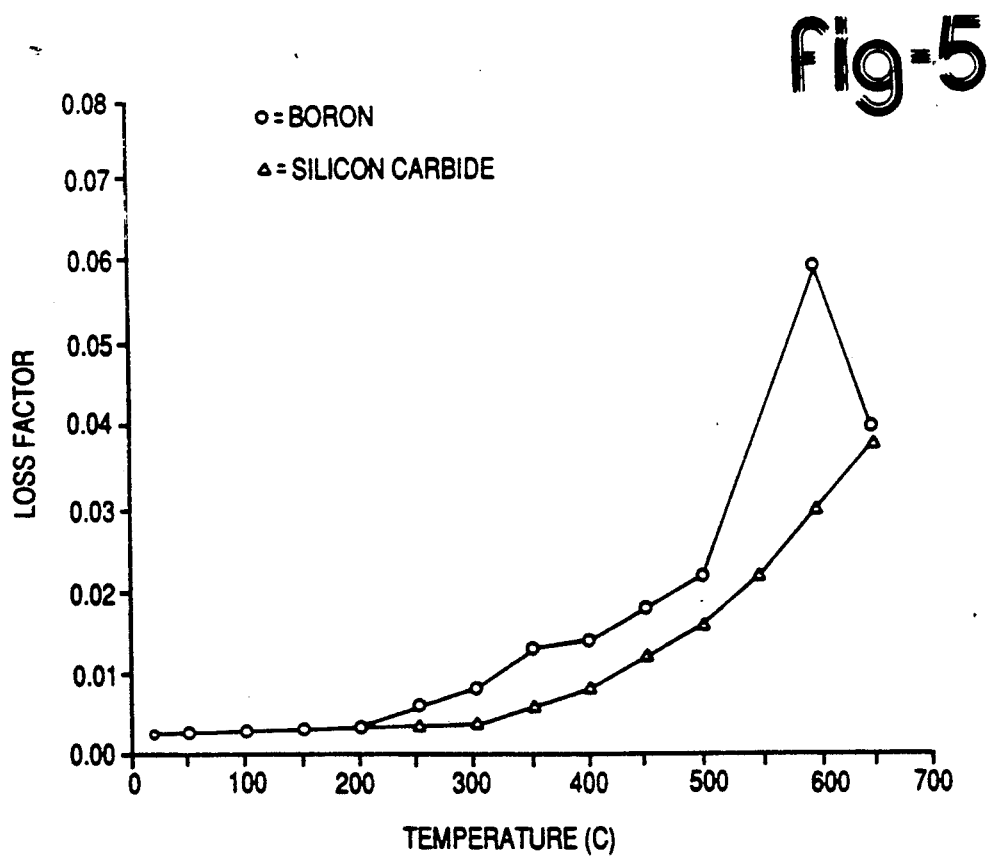

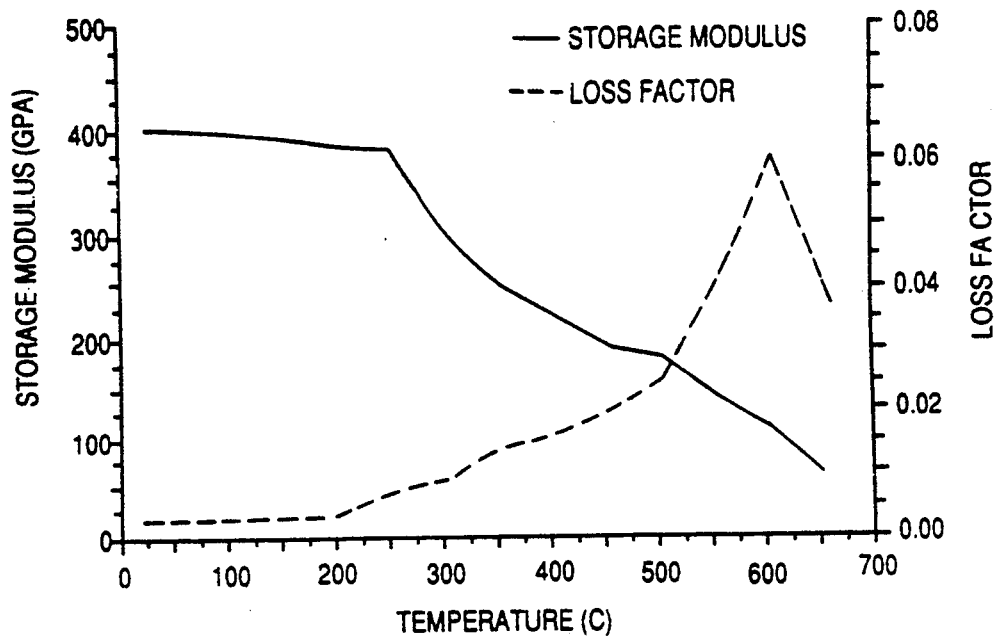
fig-6
fig-7
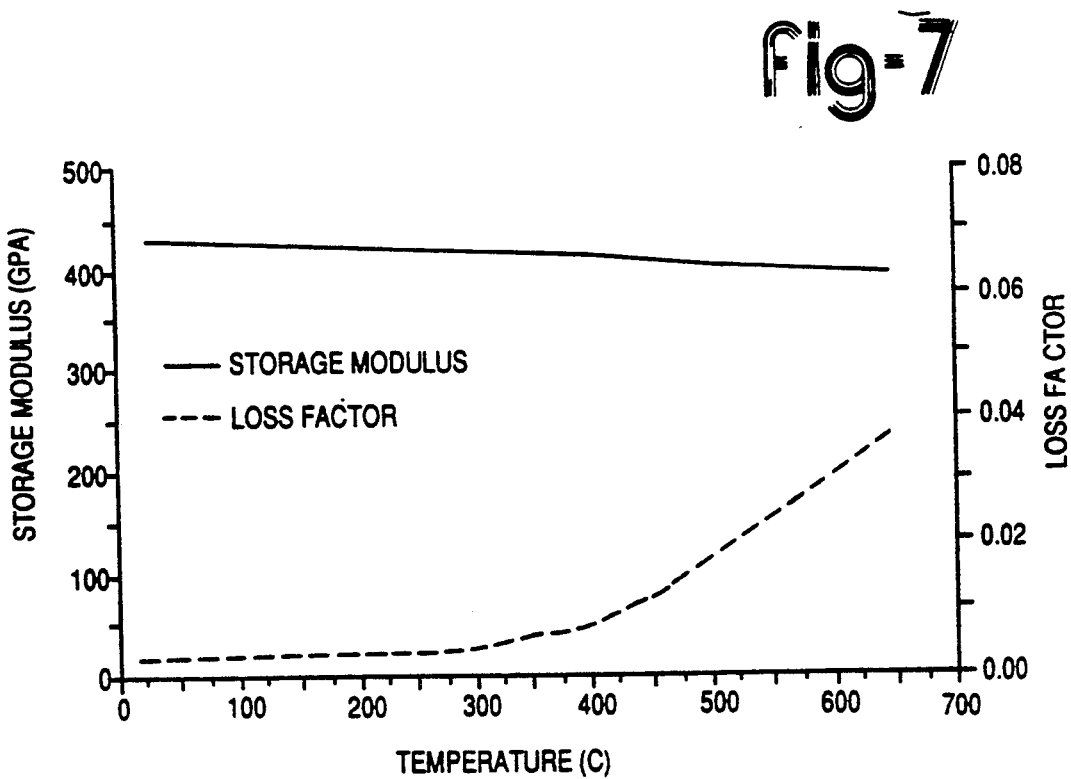

APPARATUS AND PROCESS FOR MEASURING MECHANICAL PROPERTIES OF FIBERS

TECHNICAL FIELD

This invention relates to an apparatus and method for non-destructive evaluation and testing of fibers for use in composites.

BACKGROUND ART

Advanced composites are a part of new generation of engineered materials that can be designed and manufactured with precisely controlled microstructure and chemistry to enhance particular material properties. Some of their unique properties are high strength-to-weight ratios, high stiffness-to-weight ratios, good wear and corrosion resistance, low density, low thermal expansion, high electrical resistivity and good fatigue resistance.

Advanced composites have tremendous potential in many civilian and military applications. Prime among these are advanced aerospace and automotive structures where the need exists for lightweight structural materials.

Fiber reinforced composites are under consideration for use in a variety of automotive and aerospace applications, where they must operate in a vibratory environment. Since these materials may enhance noise and vibration attenuation, it is important that the dynamic mechanical properties (i.e., internal damping and dynamic stiffness) of these materials be characterized. However, a review of composites literature shows that although static properties such as strength and fracture toughness have received considerable attention, the dynamic mechanical properties have not received the same level of attention.

Knowledge of mechanical properties of composites and their constituents is fundamental to analyses and design of fiber composite structures. Though some of these properties are determined by physical experiments, several of them are not readily amenable to direct measurement by testing. In addition, testing is usually time consuming and costly. Composite specimens with specific configurations must have been made prior to testing. Furthermore, parametric studies of the effect of fiber volume ratio on various properties can be made only by conducting an extensive series of tests.

Linear elastic composite micromechanics has been used in the past to derive equations for predicting elastic constants of composites based on the corresponding constituent (fiber and matrix) properties. Linear viscoelastic micromechanics has been used to predict dynamic mechanical properties such as damping and dynamic modulus. Equations derived from such studies provide a quantitative insight into the behavior of composites. The various equations can be used to conduct parametric studies as well as sensitivity analyses to assess the effects of using various constituent materials.

Due to the difficulty in measuring fiber properties, such properties have been inferred by substituting measured composite and matrix properties into theoretical micromechanics models. It is evident that accurate properties of the constituents are required to predict composite properties using micromechanical equations. However, very little information is available regarding fiber properties and experimental methods used to measure these properties as a function of temperature. This is particularly true for dynamic mechanical properties.

Characterization of the vibration damping properties of fiber reinforced composites is important for several reasons. In order to design materials with predetermined damping, strength and stiffness properties, it is necessary to measure the dynamic mechanical properties of the composite constituents. Damping in composites involves a variety of energy dissipation mechanisms which depend on vibrational parameters such as frequency and amplitude and environmental conditions such as temperature and moisture. Generally speaking, fibers used for reinforcement of structural composite materials are the primary source of composite stiffness. Thus, data for such fiber properties as dynamic modulus and damping are required by design engineers to understand and predict the dynamic response of composite materials that are subject to impact and vibratory loading. In addition, damping measurement can be a very sensitive non-destructive evaluation tool for understanding and monitoring damage, defects, degradation and time-dependent deformation mechanisms within a material's microstructure.

Test methods for the measurement of mechanical properties of high modulus reinforcing fibers are not as well developed as the corresponding test methods for high modulus composites. For example, the only published standard appears to be ASTM D3379, which describes the static test method for determining longitudinal tensile strength and Young's modulus of single-filament materials.

Single filament experimental techniques to determine interfacial shear strength and failure mode in composite materials have been developed. Kawabata has developed new equipment for the static measurement of longitudinal, transverse and shear moduli of single fibers up to about 400° C. Kawabata, S., "Measurements Of Anisotropic Mechanical Property And Thermal Conductivity Of Single Fiber For Several High Performance Fibers", 253-262, Pro. 4TH Japan—U.S. Conference on Composite Materials, Technomic Pub. Co., Lancaster, Pa. (1989).

Information on dynamic mechanical testing of fibers at elevated temperatures appears to be very scarce. The dynamic extensional modulus of fibers has been measured using forced vibration, non-resonance methods. The principle of these techniques is to apply a sinusoidal extensional strain to the specimens, and simultaneously measure the stress. The viscoelastic behavior is then specified from the relative amplitudes of the stress and the strain, and from the phase shift between them.

DiCarlo, J. A. and Williams, W., "Dynamic Modulus and Damping of Boron, Silicon Carbide and Alumina Fibers," NASA TM 81422:E345 (1980) have developed a cantilever fiber test to measure the dynamic flexural modulus and damping of boron and silicon fibers in flexural vibration up to 800° C. The basic test technique consists of the forced flexural vibration of cantilevered fibers in a high-vacuum cryostate furnace. The tests were conducted in vacuum to eliminate air damping due to large amplitude of fiber specimens when excited. The test specimens were clamped between two stainless steel plates that contained indentation grooves to clamp fibers of various diameters. Dynamic modulus was calculated from the resonant frequencies at which maximum specimen amplitude was observed. In this study, the flexural damping capacity, which is the percentage of stored mechanical energy lost to heat per cycle of specimen vibration, was determined by disconnecting vibrations to freely decay.

The need to experimentally determine the dynamic mechanical properties of constituent materials of a composite in order to build and validate micromechanical models cannot be over-emphasized. From the literature survey, one can conclude that the test methods to measure dynamic properties of composite and matrix materials are well developed, while the test methods to determine dynamic properties of fibers need more attention. This is particularly true for elevated temperature testing.

In a composite, the primary function of the fibers is to support longitudinal loading, and the importance of fiber flexural properties is not clear. In the composite, the load transfer from matrix to fibers occurs by interfacial shear, and the resulting fiber stress is a longitudinal normal stress. Although the flexural vibration of fibers is an accurate test method for determining dynamic properties, one cannot assume that the results are identical to those obtained by subjecting the fibers to longitudinal vibrations along their axes. It is not possible to convert flexural into axial data mathematically without analyzing the distribution of phases within the fiber and understanding their properties.

It is clearly evident that the accurate measurement of constituent material properties as a function of temperature would result in very useful data and composite micromechanics can then be used to predict composite properties and conduct parametric studies easily. This would also mean that by using measured properties of fiber, matrix and composite in micromechanics models, the interphase properties can be deduced. Up to now, the back-calculated fiber properties have probably included interphase effects as well.

SUMMARY OF THE INVENTION

Against this background, the primary objective of the present invention is the development of an apparatus for the measurement of dynamic modulus and damping of fibers under longitudinal vibrations.

The other objective is to use the same apparatus to measure dynamic properties of fibers at elevated temperatures.

In carrying out the above objectives, a process for measuring mechanical properties of structural fibers is described. The steps comprise: suspending a fiber from a rigid fixture so that it may hang vertically therefrom; attaching a mass to a lower end of the fiber so that the fiber is in tension; guiding the mass in a frictionless manner to avoid extraneous damping, so that only extensional motion of the fiber is permitted; exciting the mass and the fiber with a longitudinally directed impulse to induce an amplitude of extensional vibration that is sufficiently small to avoid buckling of the fiber; generating output signals according to the impulse that excites the mass and the fiber, and the vibration response according to the vibration induced in the fiber by the impulse; communicating computing means with the output signals, the computing means being adapted for storing data for deriving certain material properties of the fiber based upon the output signals; and displaying at least one signal representative of the material properties.

An apparatus is also described for non-destructive evaluation and testing of structural fibers. The apparatus comprises a rigid end fixture attached to the apparatus for securing a fiber thereto. A mass is suspended vertically from a lower end of the fiber so that the fiber is in tension. A means for guiding the mass is disposed thereabout in a frictionless manner to avoid extraneous damping, so that only extensional motion of the fiber is permitted. Also provided is a means for exciting the mass and the fiber with a longitudinally directed impulse to induce an amplitude of extensional vibration that is sufficiently small to avoid buckling of the fiber. An excitation sensor lies in communication with the excitation means, the excitation sensor being capable of generating an excitation signal in response to the impulse that excites the mass and the fiber. A vibration sensor is provided in non-contacting communication with the mass, the vibration sensor being capable of generating a vibration signal in response to the vibration induced in the fiber by the impulse. Computing means are communicated with the output signals, the computing means being adapted for storing data for deriving certain, material properties of the fiber based upon the output signals, and displaying at least one signal representative of the material properties.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 4 is a graph illustrating the variation of storage modulus for boron and silicon carbide fibers with temperature;

FIG. 5 is a graph illustrating the variation of the damping loss factor for boron and silicon carbide fibers with temperature;

FIG. 6 is a graph illustrating the temperature dependence of storage modulus and loss factor for boron fibers;

FIG. 7 is a graph illustrating the temperature dependence of storage modulus and loss factor for silicon carbide fibers.

DETAILED DESCRIPTION OF THE PREFERRED EMBODIMENT

Figure 1:
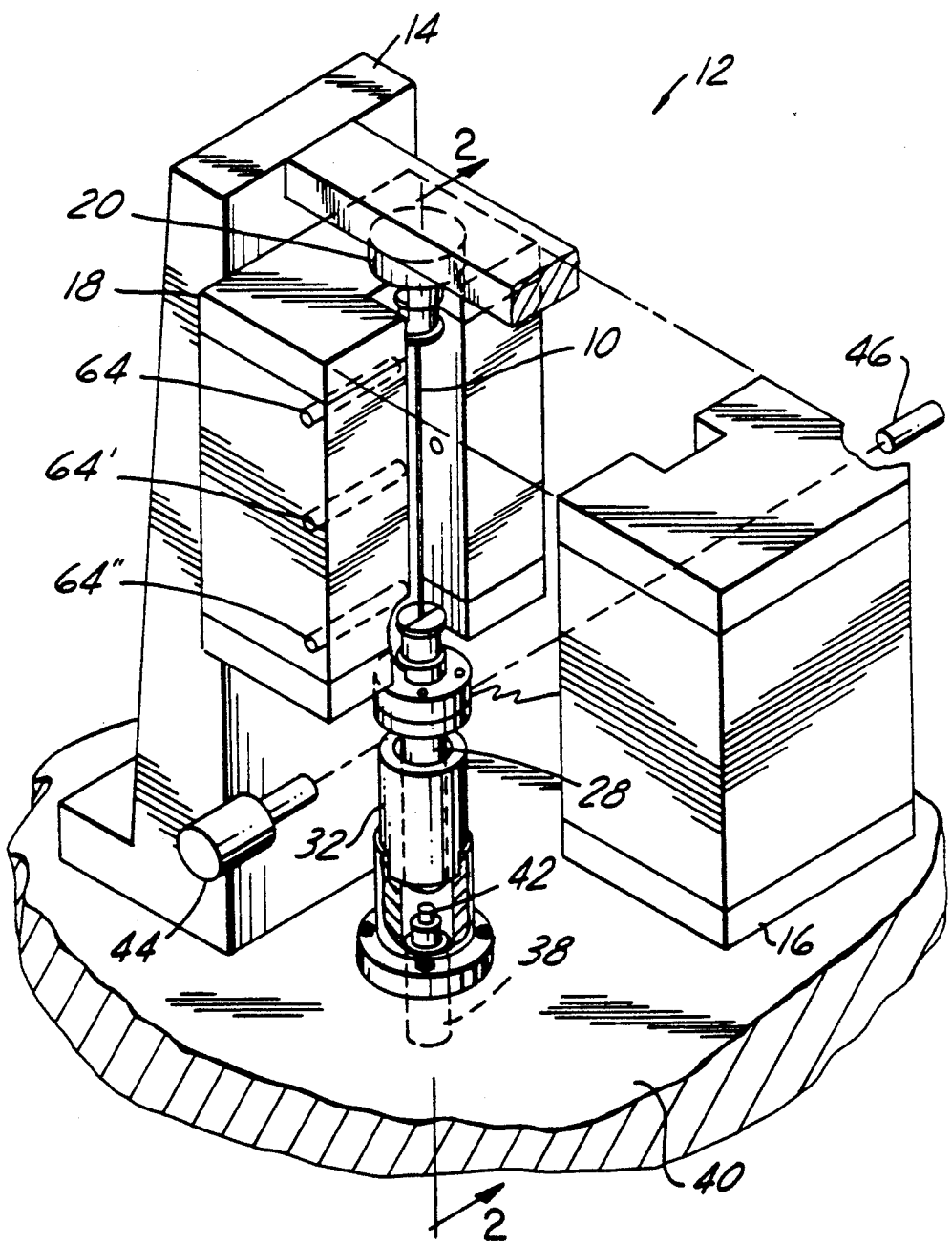
FIG. 1 depicts an apparatus for non-destructive evaluation and testing of reinforcing fibers according to the present invention with a section of a support stand broken away for clarity.
Figure 2:
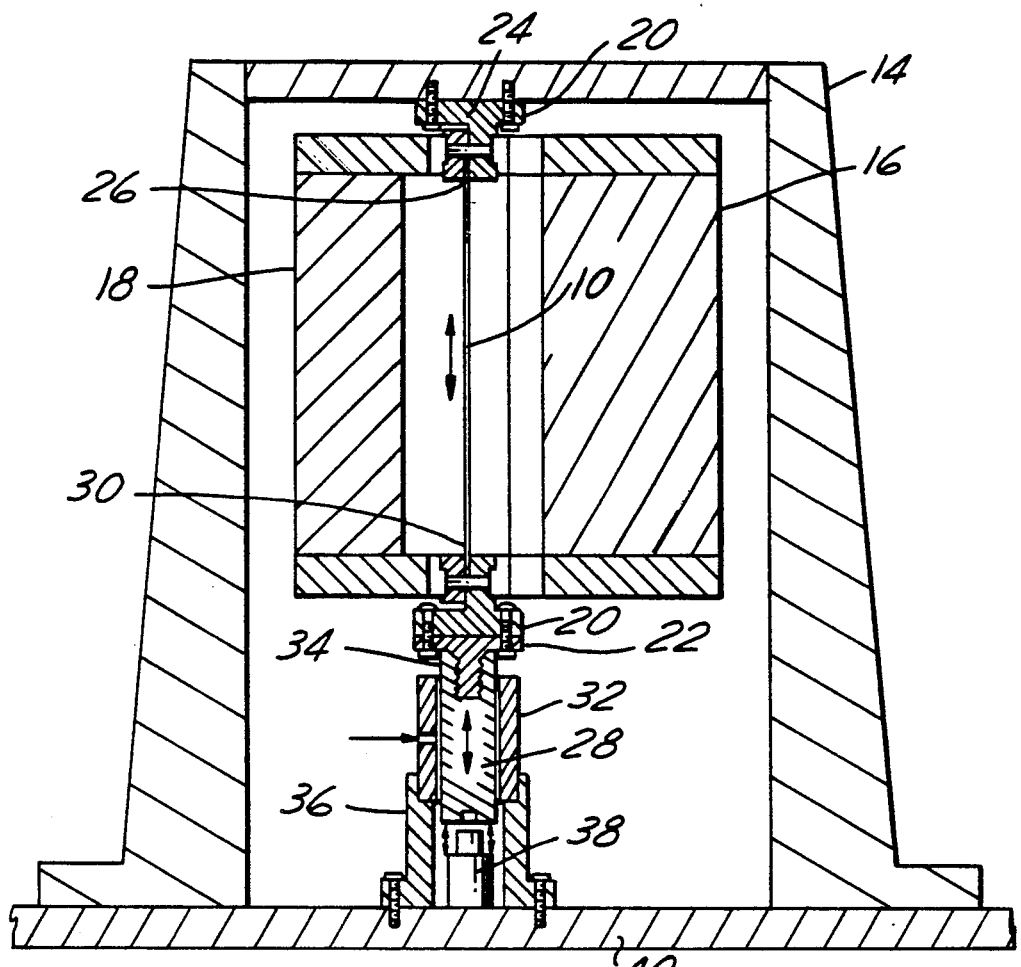
FIG. 2 is a cross-sectional view of the apparatus taken along the line 2—2 of FIG. 1.

According to the present invention, as shown in FIGS. 1-2, an apparatus 12 is disclosed which involves extensional vibrations of a fiber specimen 10. The apparatus 12 is used to measure the storage modulus and damping loss factor of fibers and is based on a single degree of freedom vibratory system consisting of a mass 28 suspended from the fiber specimens. As shown in any vibrations textbook, the parameters describing the vibration response of such single degree of freedom spring-mass-damper systems may be used in reporting damping test results. The damping parameters may be estimated by curve-fitting to the measured response of material specimens in either free or forced vibrations if a single mode can be isolated for the analyses.

Figure 8:
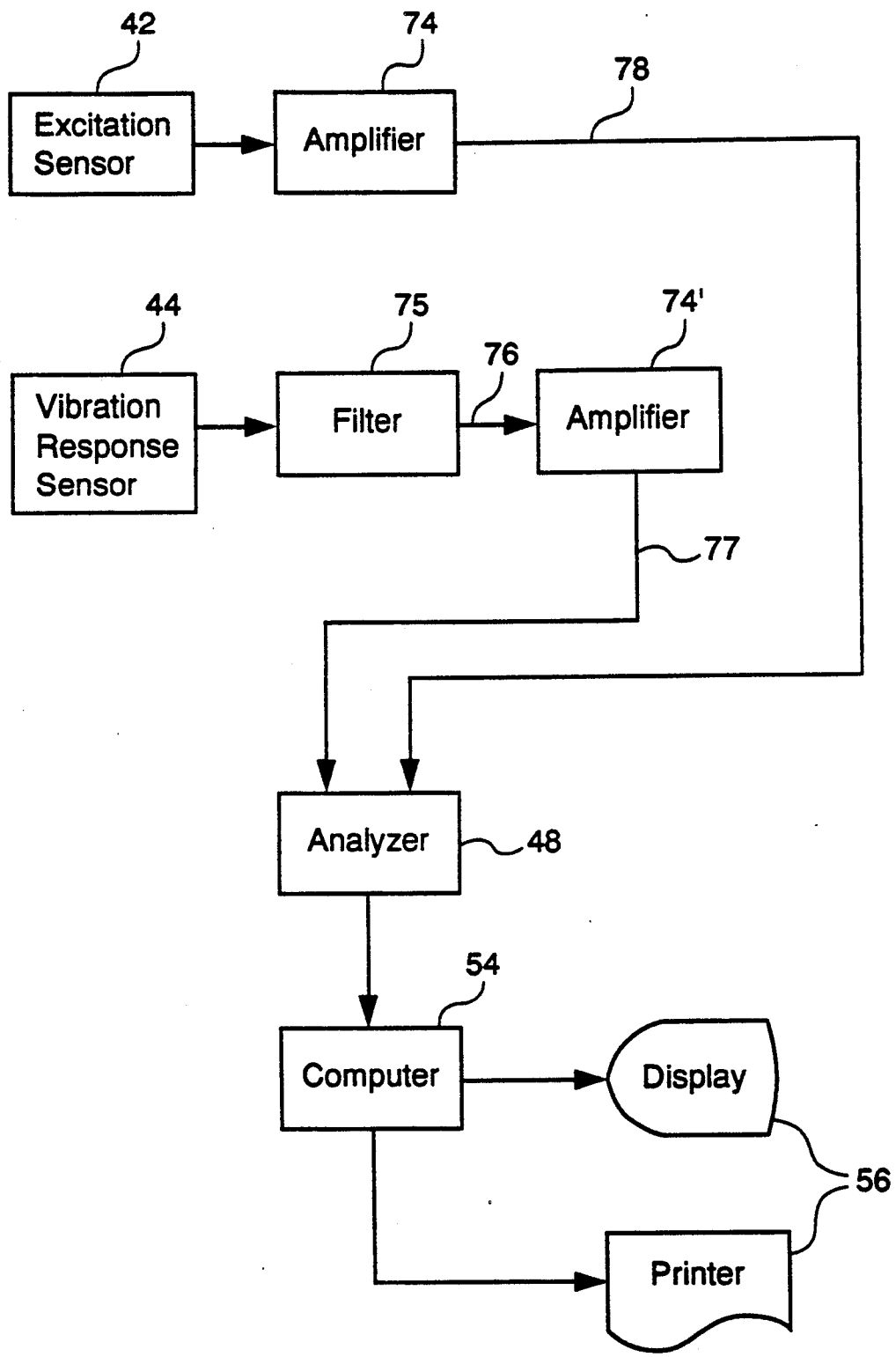
FIG. 8 is a signal flow diagram of components used in the present invention.

An impulse frequency response technique is used to test fiber materials at room temperature. The experimental technique consists of longitudinal excitation of the specimen with an impulse obtained from a remotely mounted electro-magnetic hammer 38 that has a force transducer or excitation sensor 42 attached to its tip (FIG. 8).

The electromagnetic hammer 38 is used to minimize variability of the excitation in successive measurements due to differences in the input force and the striking angle, giving a more reproducible impulse. In the fiber tests disclosed herein, it is also possible to reduce the input force so that the resulting specimen amplitude is small enough to avoid fiber compression and possible fiber buckling. A smaller force and thus smaller amplitudes will considerably minimize air damping. However, the force signal is still strong enough to trigger the data acquisition system, which is based on a Fast Fourier Transform (FFT) frequency spectrum analyzer 48 (FIG. 8).

The resulting vibratory response is monitored by a remote electro-optical displacement follower, or other non-contacting vibration sensor 44. This system can also be used to measure fiber specimen vibrations even when the tests are conducted at high temperatures.

Input and output signals are analyzed by the frequency spectrum analyzer/data acquisition and reduction system 48 that has been adapted for curve-fitting to the frequency response function.

Figure 3:
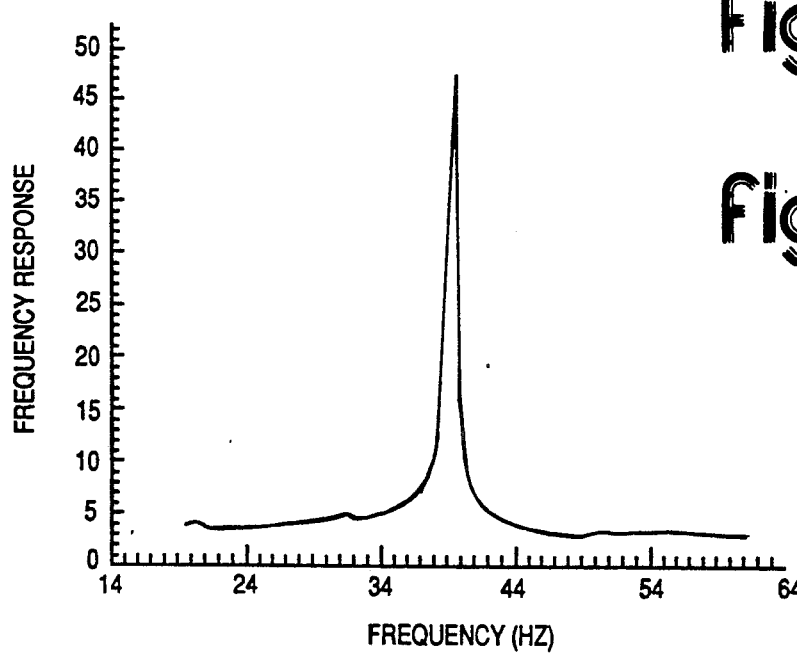
FIG. 3 is a typical frequency response curve from a fiber test.

A typical frequency response curve for fiber tests at room temperature is shown in FIG. 3. A computer program reads the binary values from the memory of the FFT analyzer 48, makes the corresponding transformations to the current scale, finds the points on either side of the half-power points, and calculates the half-power points by interpolation. The conventional "half-power bandwidth" method is then applied on the appropriate peak in the frequency response spectrum (FIG. 3). The resonant frequency and the half-power bandwidth are used to find the loss factor:

$$\eta_f = \frac{\Delta f}{f_1} \tag{1}$$

where, $\eta_f$ = Fiber extensional loss factor
$\Delta f$ = Bandwidth at the half power points
$f_1$ = Resonant frequency of the single degree of freedom fiber/mass system The frequency equation for the single degree of freedom spring-mass-damper system is used to determine the storage modulus of fiber specimens as shown in Equation (2) below. This equation assumes that the mass of the fiber specimen 10 is negligible.

$$E_f = \frac{4\pi^2 f_1^2 L_f M}{A_f} \tag{2}$$

where, $E_f$ = Young's modulus (or extensional modulus) of the fiber
$L_f$ = Free length of the fiber
$M$ = Suspended mass
$A_f$ = Cross-sectional area of the fiber.

The complex fiber modulus $E_f^*$ is then derived from the measured values for damping loss factor and storage modulus using Equation (3) as follows:

$$E_f^* = E_f(1 + i\eta_f) \tag{3}$$

where $i = \sqrt{-1}$ = imaginary operator

The disclosed apparatus 12 involves a novel application of the previously described impulse frequency response technique and is based on the fundamentals of vibrations presented above. One version of the new apparatus 12 involves extensional vibration of fiber specimens 10.

The fiber specimens are mounted inside a quartz lamp heater assembly 16, which controls the temperature from ambient to 1400° C. An appropriate ceramic insulation box 18 closes the heater assembly 16 on the opposite side to avoid undue heat loss.

A remotely mounted instrumented hammer 38 is used to excite the specimen 10 impulsively, and the resulting vibratory response is monitored by the remote electro-optical displacement follower or other non-contacting vibration sensor 44. Input excitation signals 78 and vibratory response signals 76 are analyzed by the frequency spectrum analyzer (FFT analyzer) 48 and computing means 54 (FIG. 8) for curve-fitting to the frequency response function (FIG. 3).

Ceramic fixtures 20 (FIG. 2) clamp the fiber specimens 10. An air bearing 32 is used for the fiber test to ensure single degree of freedom motion of the system. Thermocouples 64, 64', 64" are used to measure specimen temperatures at three different locations over the lengths of the specimens.

It is desirable to have the entire length of the fiber specimen 10 in the heated zone of the quartz bulb heater 16 to reduce the possibility of any thermal gradient over the specimen length. The quartz bulb heater 16 has three zones that can be individually controlled to achieve this objective. A thermal gradient over the fiber length would give misleading results.

The test apparatus is also designed to test fiber bundles, composites and matrix materials for similar properties at elevated temperatures.

In order to use the extensional vibration concept for a single degree of freedom system, it is essential to suspend the fiber specimens using a predetermined mass 28. The frequency of extensional vibration of the fiber specimens can be deduced from Equation (4) as follows:

$$f_1 = \frac{1}{2\pi} \sqrt{\frac{A_f E_f}{L_f M}} \tag{4}$$

As observed from Equation (4), a decrease in the dynamic modulus results in a reduced frequency of vibration for a given mass 28, length and cross sectional area of the fiber 10. The only problem with the FFT analyzer 48 at low frequencies is that the time required to do the FFT calculation is very long.

Accordingly, the frequency of flexural vibration in all cases was desired to be above 25 Hz. The lesser the fiber thickness, the lower the frequency of vibration. A very low fiber modulus would also result in a low frequency of vibration. Thus, using a fiber thickness of 1.6 mm and the smallest anticipated fiber modulus of 70 GPa, it was observed that a specimen length greater than 183 mm would result in a frequency of Vibration less than 25 Hz. Preferably, fiber thickness should be in the range of about 1.5 mm–2.0 mm, and its length less than or equal to 180 mm.

Having fixed the length of the specimens to be about 183 mm (heated length), it was then required to determine the suspended mass 28 for fiber tests from Equation (4). The fibers were to be tested in tension and buckling had to be avoided during experiments. A very small mass 28 would result in higher frequencies of vibration, but the impulse supplied to vibrate the specimens might subject the fibers to compression. On the other hand a larger mass 28 would result in the breaking of certain fibers due to possible strength reduction at elevated temperature, but the impulsive force would not cause the fibers to go into compression. A weight of about 5.34 Newtons (1.25 lbs) was found to comply with the various requirements.

The multi zone heater 16 is designed for ultra-high temperature testing of fibers, composites, metals and ceramics (Refer to Table 1 for manufacturer's address). The heating elements can be controlled individually or in groups to compensate for end of specimen grips, or other phenomena that can cause non-uniform temperature distribution. Each of the three zones in the heater 16 contains two infrared lamps and is individually controlled by an external power controller. Single phase zone controllers are suitable for use with both resistive and inductive loads.

The quartz bulb heater 16 end seals are air cooled. The reflector body and heater 16 frame are cooled by water. Gas ports offer the capability of using inert gas to accelerate specimen cooling. A lamp element has very little mass and heats up very quickly. The ability to heat up specimens very fast and the capability to control the power to the heated zones over the length of the specimens to minimize any thermal gradient are the significant advantages this type of assembly has over the conventional laboratory furnaces.

The quartz bulb heater 16 includes safety systems to prevent damage and losses. Since specimens are to be tested up to 1400° C., air flow and water flow to cool the heater bulbs and the aluminum casing attains very high significance. Thus, air flow and water flow sensors are inserted in the respective paths, to ensure a constant supply of both air and water. Three circuit breakers, one for every independent heater zone power controller are provided. Air and water flow relay switches are set up to trip all the three circuit breakers, thereby cutting off power to all the quartz bulb heater zones in the event of any inadvertent air or cooling water flow irregularities.

A built-in thermostat in the heater 16 assembly also trips the main circuit breaker at some predetermined critical temperature. In addition, to avoid any damage due to accumulation of moisture in the heater 16, a self-contained air dryer unit with air filters has been used. This was necessary because ambient air supply may be impure and damp.

The insulation box (Refer to Table 1 for manufacturer's address) comprises the other half of the box is made high purity alumina fibers bonded in alumina matrix. The material of construction is known to have very high strength, low density, low thermal conductivity and considerable immunity to thermal shock. The insulation box has been made in three pieces attached together with alumina cement and is fairly machinable. The top and bottom pieces of the insulation box are identical. The center piece is attached to the end pieces by means of dowel pins and alumina cement.

The box is designed in order to permit temperature measurements of the specimens at three different locations along the length of the specimens. In addition, holes drilled in either side of the box facilitate optical response measurements. The location of these holes are such that they do not focus on any vibrational nodes for beam specimens ranging from 127 to 183 mm. The top and bottom ends of the box have recesses made to accommodate ceramic fixtures 20 and to make the overall assembly easier.

A fiber specimen rigidly fixed at the top end and freely suspended with a mass 28 at the other end would obviously move in all directions when vibrated using an impulse. It is essential to guide the system to permit only the vertical motion and eliminate all other motions. However, it is also important to design such a system without any mechanical or frictional losses, in order to avoid extraneous damping.

A commercially available air bushing 32 (refer to Table 1 for manufacturer's address) was modified for this application. The air bearing 32 is made of a stainless steel jacket and a special type of bronze bushing. Air under pressure is supplied through the jacket. The bushing is specifically developed for porosity and lets the supply air pass through to the inside from all around the periphery. A stainless steel shaft slightly longer than the air bushing was fabricated. The diametrical clearance between the shaft and the bushing is precisely controlled to about 0.038 mm because this clearance determines the air flow and outlet.

The air bushing completely eliminates horizontal motions in all directions and makes it easier to monitor specimen response during fiber tests using the electro optical displacement follower. The air bearing 34 shaft is attached to the lower end 30 ceramic fixture.

Ceramic fixtures 20 clamp the fiber specimens at either end (refer to Table 1 for manufacturer's address). Both the upper end and lower end fixtures 20 are identical and specifically designed to be a two-piece construction. Consistent with the single degree of freedom concept, the top end fixture was rigidly fixed and the lower end 30 fixture contributing to the end mass 28 was bolted to the stainless steel shaft of the air bearing 32 using an intermediate coupler. The coupler is made of mild steel and bolts on to the circular flange of the ceramic fixture 20 at one end while it is screwed into the stainless steel shaft of the air bearing 32 at the other end.

As mentioned earlier, the desired end weight was calculated to be about 5.34 Newtons (1.25 lbs). The use of a steel shaft in the air bushing prescribed additional constraints in the selection of fixture material since the shaft and the lower end 30 fixture make up the total end mass 28.

The fixtures are made of 99.5% alumina because they remain stable at elevated temperatures, have a high modulus of elasticity and low density. The fixtures have a glazed finish so that they reflect heat when exposed to radiative energy in the quartz bulb heater 16. Although many ceramics can withstand such high temperatures, this material was used because very high precision machining of the two flat surfaces (0.05 mm flatness) was desired in order to clamp all sizes of fibers. The two flat plates of the fixtures are bolted together by a stainless steel bolt. Holes are drilled in the middle of the bolt shank to allow the fiber specimens to pass through. This is thought to ensure better clamping in the fixtures over the entire length of the plates.

To determine temperature dependency of the dynamic modulus and damping loss factor, the temperatures of the specimens have to be measured accurately. It was required to measure the specimen temperature at different locations over the length of the fibers, so that the individual heater zone controllers can be adjusted to obtain uniform temperature distribution. Unsheathed fine gage thermocouples 64, 64', 64'' with beaded junctions are used to probe the specimen surface at three locations (refer to Table 1 for manufacturer's address). These Platinum-Rhodium thermocouples with a wire diameter of about 0.254 mm are not affected by radiation and can be used in an oxidizing atmosphere up to about 1500° C. Pure alumina ceramic capable of withstanding very high temperatures is used as thermocouple insulators. A suitable multi-channel readout device is used to record the measured temperatures.

The non-contacting optical displacement follower 44 (refer to Table 1 for manufacturer's address) is used for motion and vibration measurement, thereby not loading the specimen or changing the specimen dynamics in any way.

The system includes an optical displacement follower 44 (FIG. 8) and a conditioning unit (filter 75, the follower 44 which can track the motion of a target along any particular axis. The target to be studied must have a sharp discontinuity in the intensity of light being emitted from it. It is this light-dark interface that is actually being locked onto by the tracker. The lens system takes the image of this discontinuity and focuses it onto the photo cathode of an image dissector tube. The number of electrons emitted from the photo cathode is proportional to the intensity of the projected light. This electron density enters the small aperture and is amplified to give a proportional current output which is then calibrated as a measure of displacement.

The target monitored by the optical system in the fiber test is the circular flange of the lower end 30 ceramic fixture 20. The targets are illuminated using a fiber optic illuminator 46 with regulated DC power supply. A vibration signal 76 (FIG. 8) represented by the output voltage from the signal conditioning unit 75 is generated and is directly proportional to target displacement. This signal 76 is fed into the amplifier 74', which generates an output signal 77 that is fed into the FFT analyzer 48 as indicating specimen response. Together, the vibration signal 77 and the excitation (input) signal 78 comprise output and input signals respectively which are communicated to the analyzer 48.

The thermocouples are calibrated using cantilever beam specimens of known temperatures. The measurement of fiber temperatures has been difficult because the fibers are very small in diameter. There should not be any contact between the specimens and thermocouple beads during experiments because of possible extraneous damping of the specimen as it vibrates due to the impulsive force.

The three zones in the quartz bulb heater 16 are controlled individually by independent power controllers, as described earlier. The thermocouples are first used to measure the temperatures of the fiber specimens at three different locations for various settings of the three zone power controllers. The temperatures of the fiber specimens corresponding to the different settings of the power controllers are measured and recorded. As expected, the end portions of the fibers are at a lower temperature level at all times because the fixtures behave as heat sinks. The end zone controllers are then appropriately adjusted with respect to the middle zone controller to get uniform temperature over the fiber length.

The thermocouples are removed during vibration tests, and the heater controller settings corresponding to the required temperatures are used. Thus, the thermocouples and the individual heater zone controllers are pre-calibrated for each material.

A lens system on the electro-optical sensor with a fixed focal length of 127 mm is used for fiber testing. Based on the full scale measurement range and the focal length of the lens, the actual working distance (between the original tracker and target) is determined as per the manufacturer's manual.

The electro-optical displacement tracker is calibrated to obtain the desired levels of light intensity for the system as recommended by the manufacturer. A digital volt-meter attached to the output on the control unit and a static calibrator (micrometer) are used for this purpose. Lock-on controls on the control unit, light source and/or high voltage to the photo tube are adjusted to obtain the required light intensity. Using this light level intensity and the working distance previously determined, the ratio of target displacement to output voltage over the full scale measurement is checked for linearity. A micrometer which is also the target during the linearity check was darkened at the tip to obtain a light-dark interface. The percent linearity over a ten volt range was found to be about 0.1%. A calibration curve showing volts output verses target displacement is derived.

In operation, certain components of the test apparatus such as the optical displacement sensor, thermocouples and the individual zone controllers for the heater assembly 16 are initially calibrated. The quartz bulb heater 16 and the ceramic insulation box 18 are placed on an adjustable stand. The top end ceramic fixture 20 rigidly bolted to a steel support stand 14, the height of which is adjustable. The complete test apparatus is mounted on an isolation table 40 to minimize the effect of building vibrations.

The fiber test apparatus and the frequency response technique was initially used to measure the dynamic properties of steel, aluminum and copper wires at room temperature. Similar tests were also conducted on silicon carbide (Textron) and boron (Textron) single fibers. The tests were conducted on three samples of each specimen and the actual mean of the results obtained is listed in Table 2. The storage modulus results for all the above are in good agreement with the data from the manufacturer and other sources.

A very heavy and rigid stand 14 was fabricated in order to minimize damping losses. Steel, aluminum, copper, boron and silicon carbide fibers were again tested with this stand. In order to confirm the results, three samples of each specimen were tested and the average dynamic properties obtained for these specimens at room temperature (see Table 3).

The results show a significant decrease in loss factor for all the specimens tested in the heavy and rigid stand 14 in comparison with the results obtained with the old support stand. However, the storage modulus results are very similar, as expected. The damping loss factor values for steel and aluminum are close to the loss factor results obtained from cantilever beam tests. The damping loss factor for boron and silicon carbide fibers obtained from these tests with the new stand are also in good agreement with the axial damping data from other sources. Consistent with the theory of micromechanics, the loss factors of boron and silicon carbide fibers are smaller than those applicable to composite damping.

Preliminary tests to determine temperature dependence of dynamic modulus and loss factor for silicon carbide and boron single fibers were conducted up to about 650° C. In order to conduct high temperature tests, it was essential to avoid excessive heating of the ceramic fixtures 20 at both ends because the stainless steel bolts used to clamp the flat plates of the fixtures expand at elevated temperatures, thereby allowing the fiber specimens to slip out of the clamps. This objective was achieved by carefully inserting thin ceramic heat shields at the top and bottom end recesses of the heater assembly 16. Three samples each of silicon carbide and boron fibers were tested to confirm the results. The average of the results from these tests has been used in FIGS. 4-7.

As shown in FIG. 4, the storage modulus for boron fibers dropped considerably with increase in temperature above 250° C. In contrast to the boron results, the dynamic modulus of silicon carbide fibers remains very stable even at high temperatures.

As seen in FIG. 5, the damping loss factor for boron fibers increases gradually beyond 200° C. and quite sharply at about 500° C. and begins to drop after peaking at about 600° C. Although the damping loss factor of silicon carbide fibers does increase smoothly after 300° C., no such phenomenon is observed within this temperature range. Another interesting observation is that the damping loss factor of boron fibers has its peak value at about 600° C. by which time the storage modulus is only about 100 GPa (FIG. 6). Similar behavior of silicon carbide fibers is expected at much higher temperatures and the results from these preliminary tests seem to predict the same within this temperature range (FIG. 7). However, it has not been possible to increase the temperature above 650° C. because the fibers break at this point.

Preliminary experiments have been conducted on single fiber specimens only. It has been difficult to accurately measure the temperature of the single fibers because they are very small in diameter (0.14 mm) and the possibility of sensing air temperature during calibration cannot be overlooked. The use of fiber bundles has to some extent improved the accuracy of temperature measurements.

Thus, there has been discussed a fiber test apparatus used to measure dynamic properties of various reinforcing fibers using the described experimental technique and theory of vibrations. The measurements have been found to be very accurate at room temperature. While the accuracy of the fiber temperature measurement is not precisely known at this point, the trends at elevated temperatures predicted by this apparatus seem to be quite reasonable. Alternative methods such as fluoroptic thermometry and radiation pyrometry are under investigation. It is also possible to operate the entire apparatus in a closed control loop with the temperature sensors and the individual power controllers to conveniently obtain a desired temperature over the length of the specimens. Preliminary results indicate that with an accurate temperature measuring system, the developed test apparatus and the test method can be effectively used to measure temperature dependent dynamic properties of reinforcing fibers.

TABLE 1

List Of Manufacturers And Addresses

| PART NAME | MANUFACTURER'S NAME AND ADDRESS |
|---|---|
| Quartz Bulb Heater | Research, Inc. P.O. Box 24064 Minneapolis, MN 55424 (612) 941-3300 |
| Ceramic Insulation Box | Zircar Products, Inc. 110 North Main Street Florida, NY 10921 (914) 651-4481 |
| Air Bearing | Dover Instrument Corp. Zoo Flanders Road Westboard, MA 01581 (617) 366-1456 |
| Ceramic Fixtures | Diamonite Products 453 W. McConkey St. Shreve, OH 44676 |
| Thermocouples | Omega Engineering, Inc. 1 Omega Drive Stamford, CO 06907 (203) 322-1666 |
| Electro-optical Displacement System | Optron Corp. 30 Hazel Terrace Woodbridge, CT 06525 (203) 389-5384 |

TABLE 2

Dynamic Properties of Various Fiber Specimens Measured Using The Initial Test Setup

| FIBER SPECIMEN | FIBER LENGTH (MM) | FIBER DIAMETER (MM) | NO. OF FIBERS | DYNAMIC MODULUS (GPa) | DAMPING LOSS FACTOR |
|---|---|---|---|---|---|
| STEEL | 190.5 | 0.2413 | 1 | 192.03 | 0.00780 |
| COPPER | 190.5 | 0.3175 | 1 | 109.19 | 0.00850 |
| ALUMINUM | 190.5 | 0.2540 | 1 | 80.02 | 0.00981 |
| BORON | 190.5 | 0.1422 | 1 | 402.76 | 0.01086 |
| SILICON CARBIDE | 190.5 | 0.1422 | 1 | 420.00 | 0.00962 |

TABLE 3

Dynamic Properties of Various Fiber Specimens Measured Using A Heavy and Rigid Support Stand

| FIBER SPECIMEN | FIBER LENGTH (MM) | FIBER DIAMETER (MM) | NO. OF FIBERS | DYNAMIC MODULUS (GPa) | DAMPING LOSS FACTOR |
|---|---|---|---|---|---|
| STEEL | 190.5 | 0.2413 | 1 | 190.76 | 0.00094 |
| COPPER | 190.5 | 0.3175 | 1 | 110.58 | 0.00116 |
| ALUMINUM | 190.5 | 0.2540 | 1 | 79.48 | 0.00151 |
| BORON | 190.5 | 0.1422 | 1 | 404.33 | 0.00253 |
| SILICON CARBIDE | 190.5 | 0.1422 | 1 | 423.47 | 0.00262 |

While the best mode for carrying out the invention has been described in detail, those familiar with the art to which this invention relates will recognize various alternative designs and embodiments for practicing the invention as defined by the following claims.

What is claimed is:

1. A process for measuring mechanical properties of structural fibers, comprising the steps of:
   suspending at least one fiber from a rigid fixture so that it may hang vertically therefrom;
   attaching a mass to a lower end of the at least one fiber so that the fiber is in tension;
   guiding the mass in a frictionless manner to avoid extraneous damping, so that only extensional motion of the fiber is permitted;
   exciting the mass and the at least one fiber with a longitudinally directed impulse in relation to the at least one fiber to induce an amplitude of extensional vibration that is sufficiently small to avoid buckling of the fiber;
   generating output signals according to the impulse, and the vibration response according to the vibration induced in the at least one fiber by the impulse; and
   communicating computing means with the output signals, the computing means being adapted for storing data for deriving certain material properties of the at least one fiber based upon the output signals, and computing the material properties.

2. The process of claim 1 wherein the step of suspending at least one fiber from the rigid fixture comprises the step of suspending a plurality of fibers from the rigid fixture.

3. The process of claim 1 further comprising the step of heating the at least one fiber to a temperature up to 1400° C. before the step of exciting the mass and the at least one fiber.

4. The process of claim 1 wherein at least one fiber has a thickness of about 1.5–2.0 mm, a modulus of elasticity of about 70 GPa, a length less than or equal to 180 mm, and the mass weighs about 1.25 lbs.

5. The process of claim 4 wherein the frequency of said vibration response exceeds 25 Hz.

6. A process for measuring mechanical properties of structural fibers, comprising the steps of:
   providing means for measuring the dynamic modulus and damping characteristics of at least one fiber under extensional vibration;
   affixing an upper end of the at least one fiber to said measuring means;
   suspending a mass vertically from a lower end of the at least one fiber so that the fiber is in tension;
   disposing means for guiding the mass thereabout in a frictionless manner to avoid extraneous damping, so that only extensional motion of the at least one fiber is permitted;
   providing means for exciting the mass and the at least one fiber with a longitudinally directed impulse in relation to the at least one fiber to induce an amplitude of extensional vibration that is sufficiently small to avoid buckling of the at least one fiber;
   deploying an excitation sensor in communication with the excitation means, the excitation sensor generating an excitation signal in response to the impulse that excites the mass and the at least one fiber;
   providing a vibration sensor in non-contacting relationship with the mass, the vibration sensor generating a vibration signal in response to the vibration induced in the at least one fiber by the impulse;
   communicating an analyzer with the sensors, the analyzer providing a frequency spectrum analysis based on the excitation and vibration signals;
   communicating computing means with the analyzer, the computing means being adapted for storing data for driving certain material properties of the at least one fiber based upon the excitation and vibration signals, and computing the material properties.

7. The process of claim 6 wherein the step of affixing an upper end of the at least one fiber to said measuring means comprises the step of affixing a plurality of upper ends of a plurality of respective fibers to said measuring means.

8. An apparatus for non-destructive evaluation and testing of structural fibers, the apparatus comprising:
   a rigid end fixture attached to the apparatus for securing a fiber thereto;
   a mass suspended vertically from a lower end of the fiber so that the fiber is in tension;
   means for guiding the mass disposed thereabout in a frictionless manner to avoid extraneous damping, so that only extensional motion of the fiber is permitted;
   means for exciting the mass and the fiber with a longitudinally directed impulse to induce an amplitude of extensional vibration that is sufficiently small to avoid buckling of the fiber;
   an excitation sensor in communication with the excitation means, the excitation sensor being capable of generating an excitation signal in response to the impulse that excites the mass and the fiber;
   a vibration sensor in non-contacting communication with the mass, the vibration sensor being capable of generating a vibration signal in response to the vibration induced in the fiber by the impulse; and a computing means in communication with the excitation and vibration signals, the computing means being adapted for storing data for deriving certain material properties of the fiber based upon the feedback signals, and computing the material properties.

9. The apparatus of claim 8 further comprising a heater positioned around the fiber to allow evaluation and testing to be done at elevated temperatures.

10. The apparatus of claim 9 further comprising a temperature measuring system in communication with the heater.

11. The apparatus of claim 8 wherein the fiber has a thickness of about 1.5–2.0 mm, a modulus of elasticity of about 70 GPa, a length less than or equal to 180 mm, and the mass weighs about 1.25 lbs.

12. The apparatus of claim 11 wherein the frequency of said vibration response exceeds 25 Hz.

* * * * *